United States Patent [19]

Fischer et al.

[11] 4,100,191

[45] Jul. 11, 1978

[54] 4-(M,M'-DI-T-BUTYL-P-HYDROXY-PHENYL)-BUTYL-2-DIAMIDES

[75] Inventors: Roman Fischer, Mutterstadt; Werner Fliege, Otterstadt; Wolfgang Koernig, Mannheim; Peter Horn, Ludwigshafen, all of Fed. Rep. of Germany

[73] Assignee: BASF Aktiengesellschaft, Ludwigshafen am Rhein, Fed. Rep. of Germany

[21] Appl. No.: 743,085

[22] Filed: Nov. 18, 1976

Related U.S. Application Data

[62] Division of Ser. No. 443,822, Feb. 19, 1974, Pat. No. 4,026,952.

[30] Foreign Application Priority Data

Feb. 24, 1973 [DE] Fed. Rep. of Germany ....... 2309375
Feb. 24, 1973 [DE] Fed. Rep. of Germany ....... 2309376
Feb. 24, 1973 [DE] Fed. Rep. of Germany ....... 2309377

[51] Int. Cl.$^2$ ............... C07C 103/147; C07C 103/19; C07C 103/24
[52] U.S. Cl. ............................ 260/557 R; 260/553 A; 260/558 R; 260/559 R; 260/559 A; 260/562 A; 260/404; 260/404.5; 260/45.9 NC; 44/71; 252/51.5 A
[58] Field of Search ........... 260/557 R, 559 A, 562 N

[56] References Cited

U.S. PATENT DOCUMENTS

| | | | |
|---|---|---|---|
| 3,433,835 | 3/1969 | Müller et al. ................... | 260/562 A |
| 3,457,328 | 7/1969 | Blatz et al. .................. | 260/562 A X |
| 3,590,083 | 6/1971 | Dexter et al. ................... | 260/562 S |
| 3,683,020 | 8/1972 | Luethi et al. ................. | 260/559 A X |
| 3,706,798 | 12/1972 | Dunnenberger et al. ........ | 260/559 A |
| 3,754,031 | 8/1973 | Dexter et al. ................... | 260/559 A |
| 3,780,103 | 12/1973 | Knell ............................. | 260/559 A |
| 3,906,033 | 9/1975 | Biland et al. ................ | 260/559 A X |

FOREIGN PATENT DOCUMENTS 7,105,824  11/1971  Netherlands ................... 260/559 A

*Primary Examiner*—Daniel E. Wyman
*Assistant Examiner*—Thomas A. Waltz
*Attorney, Agent, or Firm*—Keil, Thompson & Shurtleff

[57] ABSTRACT

Novel 4-(m,m'-di-t-butyl-p-hydroxyphenyl)-butyl-2 diamides of aliphatic, araliphatic, cycloaliphatic or aromatic dicarboxylic acids which are intermediates in the manufacture of dyes, pesticides and plastics auxiliaries, particularly stabilizers for polyolefins and polyamides. When molten, they form specific solvents for alkylphenols and are perfumes or form ingredients of perfume compositions having a fruity odor.

9 Claims, No Drawings

4-(M,M'-DI-T-BUTYL-P-HYDROXYPHENYL)-BUTYL-2-DIAMIDES

This is a division of application Ser. No. 443,822 filed Feb. 19, 1974 now U.S. Pat. No. 4,026,952

This invention relates to novel 4-($m,m'$-di-t-butyl-p-hydroxyphenyl)-butyl-2 compounds.

We have found the novel 4-($m,m'$-di-t-butyl-p-hydroxyphenyl)-butyl-2 -compounds of the formula:

I,

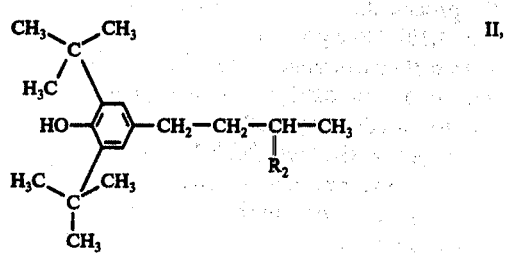

II, in which $R^2$ denotes a radical of the formula:

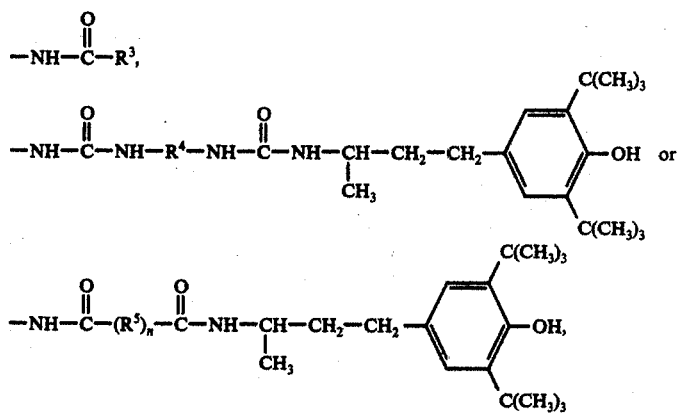

in which formulae $R^3$, $R^4$ and $R^5$ each denotes an aliphatic, cycloaliphatic, araliphatic or aromatic radical and $n$ is 0 or 1.

The novel substances may be produced by known methods, generally by reduction of corresponding butan-2-ones. Suitable starting materials are 4-($m,m'$-di-t-butyl-p-hydroxyphenyl)-butan-2-ones of the formula:

XII,

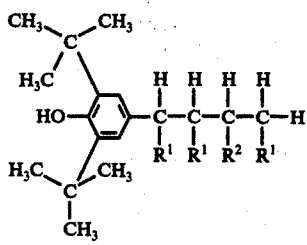

in which the radicals $R^1$ may be the same or different and each individually denotes a hydrogen atom or an aliphatic radical and $r^2$ denotes a radical of the formula:

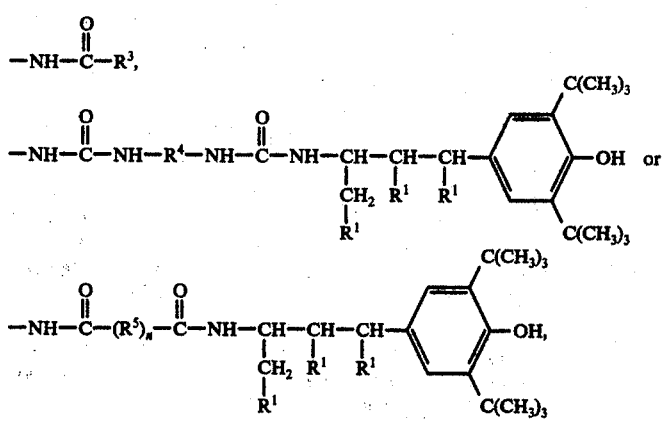

in which formulae $R^1$ has the meanings stated above and $R^3$, $R^4$ and $R^5$ each denotes an aliphatic, cycloaliphatic, araliphatic or aromatic radical and $n$ is 0 or 1.

Preferred products are the novel 4-($m,m'$-di-t-butyl-p-hydroxyphenyl)-butyl-2 compounds of the formula:

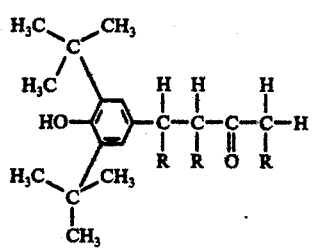

in which the radicals R may be the same or different and each denotes hydrogen or an aliphatic radical. The starting materials XII may be prepared, for example, by the process described in German Published Application No. 1,192,206 by the reaction of 2,6-di-t-butylphenol with α,β-unsaturated carbonyl compounds in the presence of a basic catalyst and an organic solvent. Manufacture is advantageously carried out by the process described in German Published Application P 23 09 370.1 by the reaction of 2,6-di-t-butylphenol with 4-hydroxybutanones-2 in the presence of a strong acid at elevated temperature.

Preferred starting materials XII and, accordingly, preferred products IV are those in the formulae of which the radicals R is the same or different and each denotes alkyl of from 1 to 4 carbon atoms or, in particular, hydrogen. The same radicals may be substituted by groups which are inert under the conditions of the reaction, for example alkyl or alkoxy groups of from 1 to 3 carbon atoms. A particularly advantageous starting material XII for the preparation of the products IV is 4-(m,m'-di-t-butyl-p-hydroxyphenyl)-butan-2-one. Other suitable starting materials XII are for example the 4-methyl-, 3-ethyl-, 1-ethyl- 1,4-dimethyl- and 1,3,4-trimethyl-4-(m,m'-di-t-butyl-p-hydroxyphenyl)-butan-2-ones.

Intermediates for the of products I are the novel 2-amino-4(m,m'-di-t-butyl-p-hydroxyphenyl)-butanes of the formula:

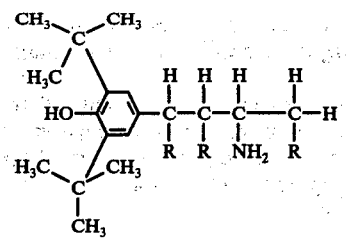

VIII, in which the radicals R may be the same or different and each individually denotes hydrogen or an aliphatic radical. A preferred product VIII is 2-amino-4-(m,m'-di-t-butyl-p-hydroxyphenyl)-butane.

The novel products VIII may be prepared by known methods, generally by reductive amination of corresponding butan-2-ones with ammonia and hydrogen. Suitable starting materials are the aforementioned 4-(m,m'-di-t-butyl-p-hydroxyphenyl)-butane-2-ones of the formula XII above.

Preferred starting materials XII and, accordingly, preferred products VIII are those in the formulae of which the radicals R may be the same or different and each denotes alkyl of from 1 to 4 carbon atoms, or, in particular, hydrogen. The said radicals may be substituted by groups which are inert under the conditions of the reaction, for example alkyl or alkoxy groups of from 1 to 3 carbon atoms. A particularly advantageous starting material XII for the preparation of the products VIII is 4-(m,m'-di-t-butyl-p-hydroxyphenyl)-butan-2-one. Other suitable starting materials XII are for example 4-methyl-3-ethyl-, 1-ethyl-, 1,4-dimethyl- and 1,3,4-trimethyl-4-(m,m'-di-t-butyl-p-hydroxyphenyl)-butan-2-ones.

Conversion by reductive amination may be represented by the following equation illustrating the use of 4-(m,m'-di-t-butyl-p-hydroxyphenyl)-butan-2-one:

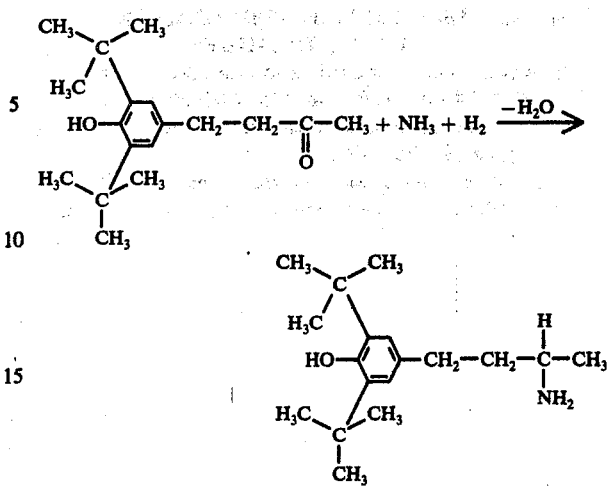

The reducing agent, advantageously hydrogen, may be used in stoichiometric amounts or, advantageously, in excess, preferably in a ratio of 1.3 to 4 moles of hydrogen per mole of starting material XII. Ammonia and the starting material XII may be used in stoichiometric amounts or the ammonia may be present in excess, usually in an excess of from 1.5 to 50 moles of $NH_3$ per mole of starting material XII. The ammonia may be used in any form, for example as gaseous or liquid ammonia, or it may be dissolved in a solvent which is inert under the conditions of the reaction.

The reaction is advantageously carried out in the presence of a hydrogenation catalyst. Suitable hydrogenation catalysts which may be used are generally one or more metals having an atomic number of from 24 to 29, usually cobalt or nickel catalysts, e.g. corresponding sintered catalysts which may contain up to 30% by weight of copper, manganese, iron and/or chromium. We prefer to use Raney nickel and Raney cobalt. The hydrogenation catalyst is usually used in amounts of from 0.5 to 50% and preferably from 1 to 10% by weight of the weight of starting material XII. Usually, hydrogen is passed into the reaction mixture at the commencement of the reaction and during the reaction at such a rate that a desired reaction pressure is maintained at the temperature at which the reaction is carried out. The reaction is advantageously carried out at a reaction pressure of from 50 to 300 and preferably from 70 to 150 atmospheres, continuously or batchwise. The reaction temperature is advantageously between 20° and 150° C and preferably between 60° and 100° C. It is also possible to use inert gases such as nitrogen, in addition to the hydrogen and ammonia, to adjust the pressure as desired.

If desired, catalysts such as ammonium chloride, ammonium acetate and acetic acid may be added in amounts of from 0.1 to 1.2% by weight of the weight of starting material XII in order to avoid the formation of by-products. Aslo suitable are catalysts which contain up to 20% by weight of aluminum oxide or magnesium oxide in addition to nickel and copper. For economical reasons alone it is preferred to use the above catalysts and not, as is possible, platinum or platinum compounds such as platinum oxide, as catalysts, at a pressure of from 1 to 3 atmospheres, advantageously with the addition of ammonium chloride.

It is advantageous to use organic solvents which are inert under the conditions of the reaction. Examples of such solvents are cyclic ethers such as dioxane and tetrahydrofuran, ethers such as glycol monomethyl ether, and preferably alkanols, advantageously of from 1 to 4 carbon atoms, such as methanol, ethanol and isopropanol. They may be fed to the reaction medium either individually or mixed with, say, each other or a starting material. In general, the solvent is used in an amount of up to 10 times the weight of starting material XII.

The reaction may be carried out as follows: The starting material XII is fed to a reactor with or without solvent, and the hydrogenation catalyst is then added and the reaction chamber is purged with nitrogen. Ammonia is then added and hydrogen is pumped in until the above reaction pressure has been reached. The reaction mixture is then heated to the above temperature and maintained at this temperature whilst further amounts of hydrogen are added until no more hydrogen is consumed by the reaction. This reaction time is generally from 2 to 3 hours. The reaction mixture is then cooled and filtered. The product is then isolated from the filtrate by usual methods, for example by fractional distillation or evaporation of the filtrate and recrystallization from ether.

The materials IV of the invention may also be converted to the corresponding 2-amino-4-($m,m'$-di-t-butyl-p-hydroxyphenyl)-butanes, e.g. the unsubstituted 2-amino compound, by reaction with ammonia at, say, from 80° to 150° C and a pressure of from 50 to 110 atmospheres. Similarly, catalytic methods of amination of hydroxyl-containing compounds may be used. For details of the execution of such amination processes, reference is made to Houben-Weyl, Methoden der organischen Chemie, Vol. 11/1, pp. 112 et seq.

The other novel materials I may be obtained by usual methods of synthesis of esters, acid amides, bis-ureas and bis-amides. To prepare esters of the formula:

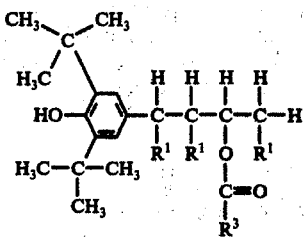

III, it is advantageous to react 4-($m,m'$-di-t-butyl-p-hydroxyphenyl)-butan-2-ols of the formula:

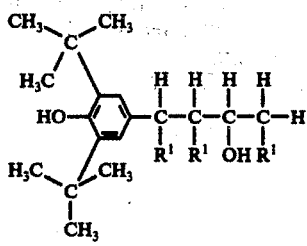

IV with carboxylic acids or derivatives of carboxylic acids of the formula:

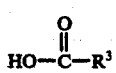

V in which $R^1$ and $R^3$ have the meanings stated above.

This reaction may be represented by the following equation illustrating the use of 4-($m,m'$-di-t-butyl-p-hydroxyphenyl)-butan-2-ol and acetyl chloride:

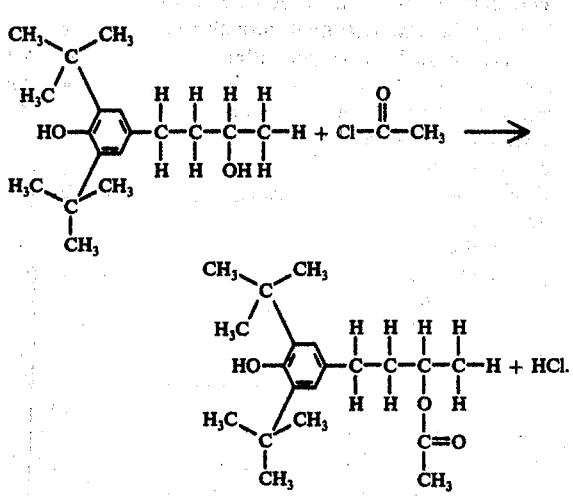

Preferred starting materials IV and V and, accordingly, preferred products III are those in the formulae of which the radicals $R^1$ may be the same or different and each denotes alkyl of from 1 to 4 carbon atoms or, in particular, hydrogen, and $R^3$ is alkyl of from 1 to 20 and in particular of from 1 to 8 carbon atoms, cyclohexyl, aralkyl of from 7 to 12 carbon atoms, naphthyl or phenyl. The said radicals may be further substituted by groups which are inert under the conditions of the reaction, for example alkyl or alkoxy of from 1 to 4 carbon atoms or nitro. A particularly advantageous starting material IV is 4-($m,m'$-di-t-butyl-p-hydroxyphenyl)-butan-2-ol. Examples of other starting materials IV are 4-methyl-, 3-ethyl-, 1-ethyl-, 1,4-dimethyl- and 1,3,4-trimethyl-4-($m,m'$-di-t-butyl-phydroxyphenyl)-butan-1-ols. Suitable starting materials V are carboxylic acids and derivatives thereof such as the halides, preferably chlorides, and single or mixed anhydrides. Examples of suitable compounds are formuic acid, acetic acid, butyric acid, palmitic acid, stearic acid, benzoic acid, cyclohexanoic acid, phenylacetic acid, naphthalene-1-carboxylic acid, napthalene-2-carboxylic acid, p-nitrobenzoic acid, p-hydroxy-$m,m'$-di-t-butylbenzoic acid, p-toluic acid, propionic acid, isobutyric acid, caprylic acid, capronic acid, lauric acid, valeric acid, (p-methoxy-i m,m'-di-t-butyl)-benzoic acid, o- and p-diethoxybenzoic acids and analogous said halides and anhydrides.

The starting material IV may be reacted with starting material V in stoichiometric amounts or with an excess of the latter, preferably an excess of from 1.1 to 1.3 moles of starting material V per mole of starting material IV. The reaction is usually carried out at temperature of from 10° to 170° C and preferably from 20° to 90° C, at atmospheric or superatmospheric pressure, continuously or batchwise. it is advantageous to use solvents such as ketones, e.g. acetone, aliphatic hydrocarbons, e.g. ligroin and hexane, ethers, e.g. dipropyl ether, tetrahydrofuran and dioxane, aromatic hydrocarbons, e.g. benzene, toluene and the xylenes, and chlorinated hydrocarbons, e.g. chloroform and methylene chloride.

Where the starting materials V are carboxylic acids, it is advantageous to use acids such as phosphoric acid, aromatic sulfonic acids such as p-toluenesulfonic acid, or, advantageously, hydrochloric and sulfuric acid, as catalysts. Advantageously, from 0.5 to 15 and in particular from 3 to 10% by weight of acid, based on carboxylic acid V, is used. If desired, materials capable of binding the water formed may also be used, e.g. anhydrous salts such as copper sulfate and iron sulfate. Also suitable are esterification catalysts such as acid chlorides, e.g. thionyl chloride, chlorosulfonic acid, ansolvoacids such as boron trifluoride, or it is possible to carry out special esterification operations such as esterification with azeotropic distillation with, say, benzene or toluene.

It is also possible to transesterify esters of the carboxylic acids V, advantageously esters with lower alkanols such as methanol or ethanol, with the starting material IV. It is advantageous to carry out the reaction with an excess of starting material IV, for example an excess of from 3 to 10 times over the stoichiometric amount of ester, with concurrent distillation of the alkanol released during the reaction. However, we prefer to use halides of carboxylic acids V, particularly the chlorides, as starting materials. If desired, they may be prepared in situ by using the carboxylic acids V together with acid chlorides such as phosphorus trichloride, phosphorus oxychloride, phosphorus pentachloride and thionyl chloride in the reaction mixture. It is preferred to react the starting materials IV with the acid anhydride or, advantageously, acid halide in the presence of pyridine, suitable amounts of pyridine being from 200 to 1,000% by weight, based on acid halide. If desired, the halide uses in this method may be prepared in situ by using an acid and, say, phosgene. The amounts of anhydride and halide and the reaction conditions are the same as those mentioned above in connection with the use of carboxylic acids. For details on the esterification reaction, see Houben-Weyl, Methoden der organischen Chemie, Vol. 8, pp. 516–549.

The reaction may be carried out as follows: A mixture of starting materials IV and V or derivatives of starting material V and, optionally, solvent, esterification catalyst, acid or pyridine is stirred at the temperature stated for from 1 to 12 hours. The ester III is then isolated in conventional manner, e.g. by mixing the reaction mixture with ice, following by acidification and extraction of the mixture with, say, benzene, and fractional distillation of the organic phase formed.

In order to prepare the acid amides of the formula:

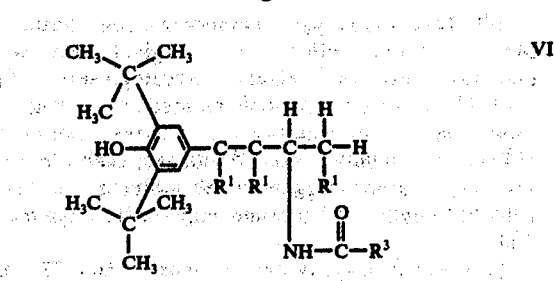

and the bis-amides of the formula:

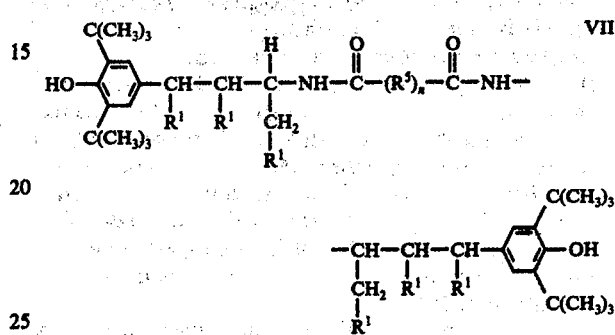

it is advantageous to use 2-amino-4-($m,m,'$-di-t-butyl-p-hydroxyphenyl)butanes of the formulae:

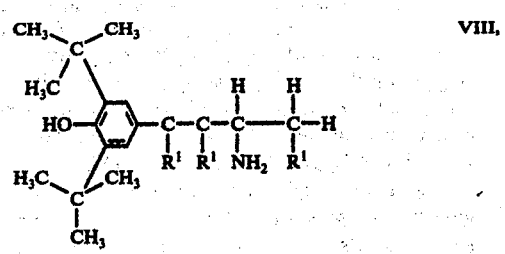

with, in the case of the preparation of acid amides, VI, the aforementioned carboxylic acids V or derivates of carboxylic acids V or, in the case of the preparation of bis-amides VII, dicarboxylic acids or derivatives of dicarboxylic acids of the formula:

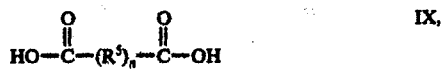

in which $R^1$, $R^3$ and $R^5$ and $n$ have the meaning stated above.

The reactions may be represented by the following equations illustrating the use of 2-amino-4-($m,m'$-di-t-butyl-p-hydroxyphenyl)-butane and benzoyl chloride or terephthaloyl chloride:

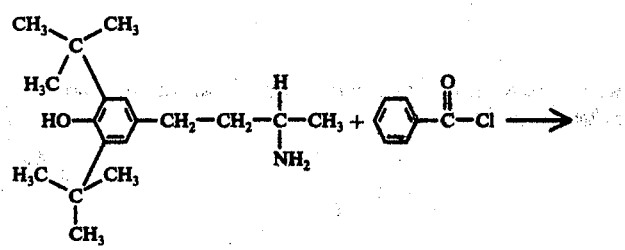

-continued

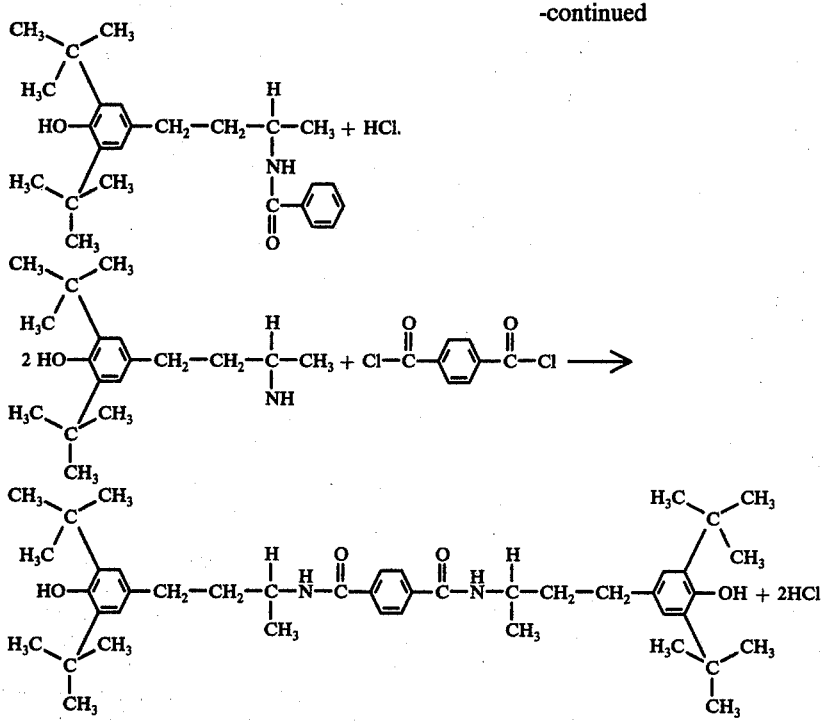

Preferred starting materials VIII, V and IX and, accordingly, preferred products VI and VII are those in the formulae of which $R^1$ and $R^3$ have the said preferred meanings and $n$ is 0 or 1, and $R^5$ denotes alkylene of from 1 to 20 and preferably of from 1 to 6 carbon atoms, cyclohexylene, aralkylene of from 7 to 15 carbon atoms, phenylene or naphthylene which may be partially or wholly hydrogenated if desired, decahydronaphthylene, benzylcyclohexylene, e.g. the radical

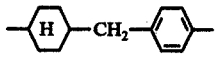

or benzylphenylene, e.g. the radical

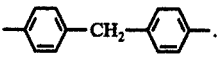

The above radicals may be substituted by groups which are inert under the conditions of the reaction, for example alkyl or alkoxy groups of from 1 to 4b carbon atoms. When $R^5$ denotes aralkylene, it may contain an arylene group and one or two alkylene groups and may thus be attached to the two adjacent carbonyl groups via one arylene group and one alkylene group or two alkylene groups.

A particularly advantageous starting material VII is 2-amino-4-($m,m'$- di-t-butyl-p-hydroxyphenyl)-butane. Examples of other starting materials VIII are 4-methyl-, 3-ethyl-, 1-ethyl-, 1,4-dimethyl-and 1,3,4-trimethyl-2-amino-4-($m,m'$-di-t-butyl-p-hydroxyphenyl)-butanes. Examples of suitable starting materials V are monocarboxylic acids and their derivatives such as halides, particularly chlorides, and anhydrides. Examples of suitable starting materials IX are oxalic acid, malonic acid, succinic acid, glutaric acid, adipic acid, pimelic acid, sebacic acid, decanedioic acid, terephthalic acid, cyclohexane1,4-dioic acid, cyclohexane-1,2-dioic acid, cyclohexane-1,3-dioic acid, napthalene-1,4-dioic acid, naphthalene-1,8-dioic acid, isophthalic acid, phthalic acid, diphenylmethane-4,4'-dioic acid, 4-(p-carboxybenzyl)-cyclohexanoic acid, tetrahydronaphthalene-1,8-dioic acid, tetrahydronaphthalene-1,5dioic acid, decahydronaphthalene-1,8- dioic acid, decahydronaphthalene-1,5-dioic acid, p-(1-carboxypropyl-2)-benzoic acid, p-(carboxymethyl)-benzoic acid and p-(carboxymethyl)phenylacetic acid. Similarly, analogous single or mixed anhydrides and dihalides, preferably dichlorides, of these acids are suitable.

The starting material VIII may be reacted with starting material V or IX in stoichiometric amounts or with an excess of starting material V, preferably an excess of from 1.1 to 1.3 moles, or of starting material IX, preferably an excess of from 0.6 to 0.8 mole, per mole of starting material VIII. The reaction is usually carried out at a temperature of from 10° to 170° C and preferably from 20° to 90° C, at atmospheric or superatmospheric pressure, continuously or batchwise. It is advantageous to use solvents such as ketones, e.g. acetone, aliphatic hydrocarbons, e.g. ligroin and hexane, ethers, e.g. dipropyl ether, tetrahydrofuran and dioxane, aromatic hydrocarbons, e.g. benzene, toluene and the xylenes, and chlorinated hydrocarbons, e.g. chloroform and methylene chloride.

As in the case of the esters, the amines VIII may be reacted with the carboxylic acid V or dicarboxylic acid IX itself or its esters. It is more advantageous to carry out the reaction with the anhydrides or, in particular, the halides, preferably the chlorides, of these acids. The acid formed during the reaction may be bound by an appropriate excess of amine or, advantageously, by the addition of bases such as caustic solutions, e.g. caustic soda, soda or terteriary amines, particularly pyridine. Suitable amounts are from 1 to 1.5 equivalents of base, based on one mole of halide of anhydride of the acids IX. Pyridine may simultaneously serve as a solvent, in which case amounts of from 1 to 1.3 moles of pyridine per mole of starting material VIII are suitable. For details on the preparation of mono- and di-carboxyamides, see Houben-Weyl, loc. cit. pp 653–660.

The reaction may be carried out as follows: The mixture of starting material VIII and the acid chloride of starting material V or IX and, advantageously, the base with or without solvent is maintained at the reaction temperature for from 0.5 to 5 hours. The product is then removed from the reaction mixture in known manner, for example by mixing with ice, acidifying the mixture and extracting it with, say, benzene, followed by fractional distillation of the extract.

To manufacture the bis-ureas of the formula and decahydranaphthalene-1,8-diisocyanates, 4-(isocyanato-benzyl)-cyclophexane isocyanate, p-isocyanatocumyl isocyanate, p-isocyanatobenzyl isocyanate and p-isocyanatophenylethyl isocyanate.

The starting material VIII may be reacted with starting material XI in stoichiometric amounts or in excess, preferably an excess of from 0.6 to 0.8 mole of starting material XI per mole of starting material VIII. The reaction is usually carried out at a temperature of from 10° to 170° C, and preferably from 20° to 90° C, at atmospheric or superatmospheric pressure, continuously or batchwise. It is advantageous to use solvents such as ketones, e.g. acetone, aliphatic hydrocarbons,

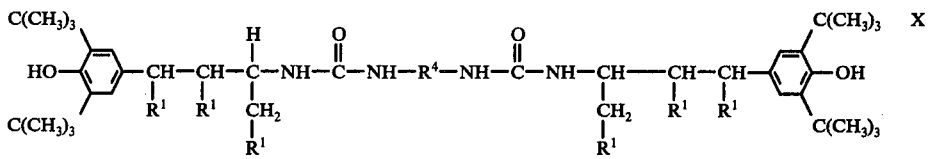 X use is advantageously made of 2-amino-4-($m,m'$-di-t-butyl-p-hydroxyphenyl)-butane VIII and diisocyanates of the formula:

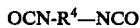 XI in which $R^1$ and $R^4$ have the meanings stated above.

This reaction may be represented by the following equation illustrating the use of 2-amino-4-($m,m'$-di-t-butyl-p-hydroxyphenyl)-butane and hexamethylene diisocyanate:

e.g. ligroin and hexane, ethers, e.g. dipropyl ether, tetrahydrofuran and dioxane, aromatic hydrocarbons, e.g. benzene, toluene and the xylenes, and chlorinated hydrocarbons, e.g. chloroform and methylene chloride. As in the manufacture of products VI and VII, it is possible to carry out the preparation of the bisureas with the addition of bases, preferably pyridine, in the manner stated. For details on the reaction of amines with diisocyanates, reference is made to Houben-Weyl, loc. cit. pp. 157 et seq.

The reaction may be carried out as follows. The mix-

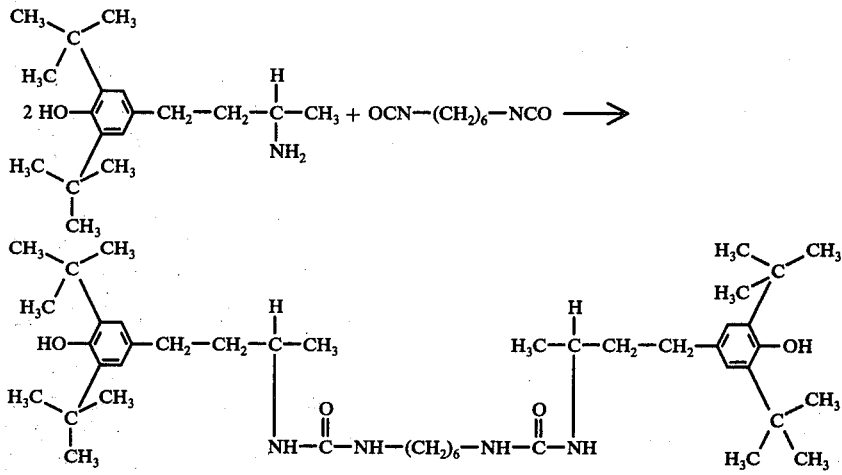

Preferred starting materials VIII and XI and, accordingly, preferred products X are those in the formulae of which $R^1$ has the above meaning and $R^4$ has the above preferred meaning given for $R^5$, the preferred radicals being substituted as indicated if desired. 2-Amino-4-($m,m'$-di-t-butyl-p-hydroxyphenyl)-butane is also a particularly advantageous starting material VIII for the manufacture of products decahydronaphthalene-but the other substances VIII mentioned above are also suitable for this reaction. Suitable starting materials XI are for example 1,4-butane-, 1,6-hexane-, p-phenylene-, 2,4-toluylene-, 2,5-toluylene-, 2,6-toluylene-, 1,5-naphthylene-, 1,8-naphthylene-, 4,4-diphenylmethane- 3,3'-dimethoxy-4,4'-diphenyl-, 3,3'-dimethyl-4,4'3,3'-diphenyl-, 1,3-propane-, 1,3-cyclohexylene-, 1,4-cyclohexylene-, m-phenylene-, tetrahydronaphthalene-1,5-, tetrahydronaphthalene-1,8-, decahydronaphthalene-1,5- ture of the starting materials with or without solvent and base is held at the reaction temperature for from 0.5 to 5 hours. The product is then isolated from the reaction mixture in the usual manner, for example by filtration or removal of the solvent and recrystallization of the residue.

The 4-($m,m'$-di-t-butyl-p-hydroxyphenyl)-butyl-2 compounds I which may be prepared in the manner described above, preferably the mono- or di-carboxamides, esters and bis-ureas of 2-amino-4-($m,m'$-di-t-butyl-p-hydroxyphenyl)-butane or the aforementioned 4-($m,m'$-di-t-butyl-p-hydroxyphenyl)-butan-2-ol IV, in particular 4-($m,m'$-di-t-butyl-p-hydroxyphenyl)-butan-2-ol, or the aforementioned 2-amino-4-($m,m'$-di-t-butyl-p-hydroxyphenyl)-butanes VIII, in particular 2-amino- 4(m,m'-di-t-butyl-p-hydroxyphenyl)-butane, are valuable intermediates in the manufacture of dyes, pesticides and plastics auxiliaries, particularly stabilizers for polyolefins. When molten, they are specific solvents for alkylphenols, e.g. 2,6-diethylphenol, 2,6-dimethylphenol, 2,4-dimethylphenol, and in the case of the amides, esters and bis-ureas including those derived from disubstituted ureas such as diphenyl urea, they form perfumes or ingredients of perfume compositions having a certain fruity odor. The aforementioned 4-(m,m'-di-t-butyl-p-hydroxyphenyl)-butan-2-ols IV, in particular 4-(m,m'-di-t-butyl-p-hydroxyphenyl)-butan-2-ol, are perfumes or ingredients of perfume compositions having an odor similar to that of bilberries, raspberries or blackberries.

Also, the products I are themselves stabilizers, aging retardants or antioxidants for organic products which can be deformed, rendered brittle, discolored or degraded in some other way by the action of heat, light, oxygen or ozone. Examples of such organic products are lubricating oils, fuel oils, oils of vegetable, mineral or animal origin, waxes, soaps, fats, gasolines, natural or synthetic rubber, natural resins and plastics such as polyolefins, e.g. polyethylene and polypropylene, (see Examples 9, 11 and 13 below).

Useful products I for this purpose are 4-(m,m'-di-t-butyl-p-hydroxyphenyl)-butyl-2 compounds of the formula:

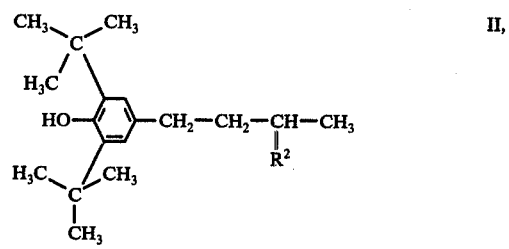

in which $R^2$ denotes amino, hydroxyl or a radical of the formula:

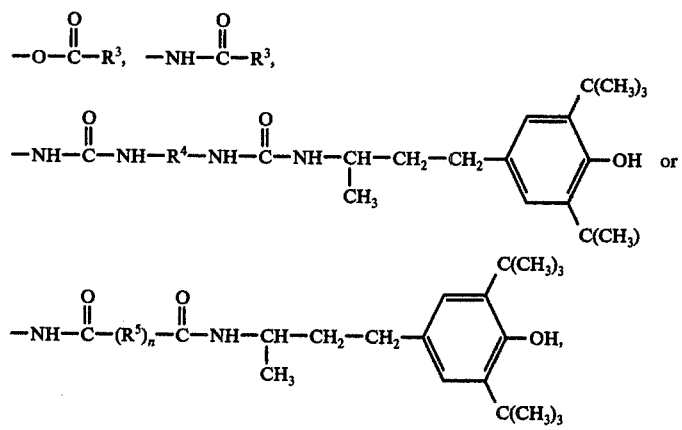

where $R^3$, $R^4$ and $R^5$ each denotes an aliphatic, cycloaliphatic araliphatic or aromatic radical and $n$ is 0 or 1. We particularly prefer products I in the formula of which $R^2$ and $n$ have the meanings stated above and $R^3$, $R^4$ and $R^5$ have the preferred meanings stated above.

Particularly advantageous products I are the following compounds: 4-(m,m'-di-t-butyl-p-hydroxyphenyl)-butan-2-ol, 2-amino-4-(m,m'-di-t-butyl-p-hydroxyphenyl)-butane and the compounds of the following formulae:

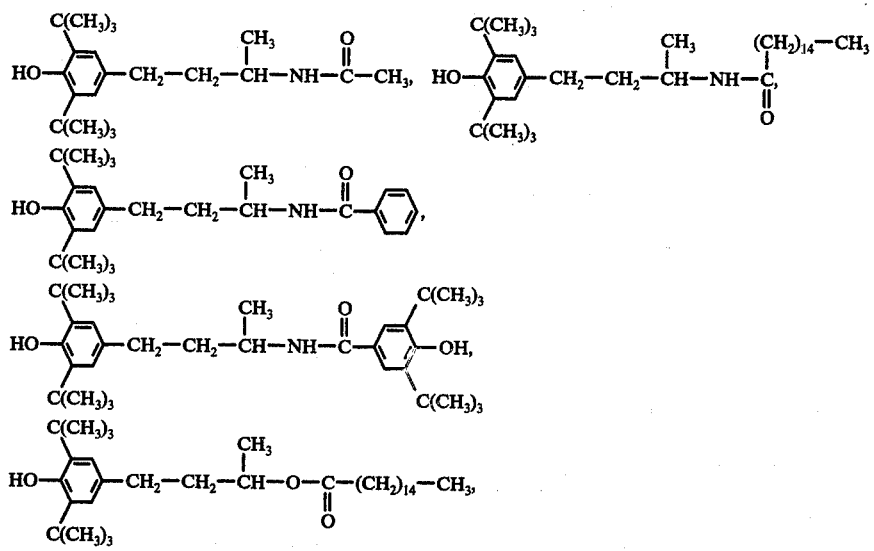

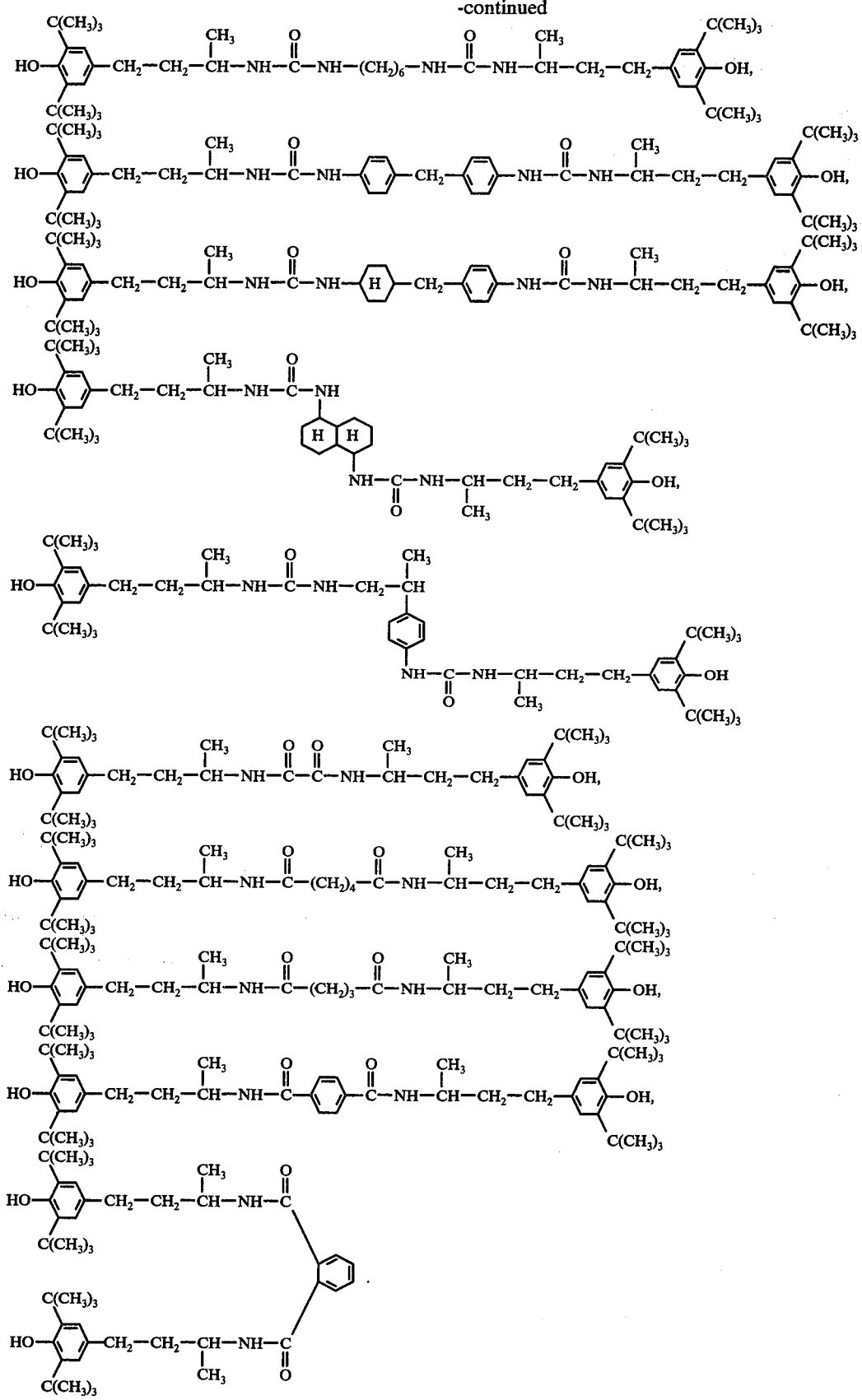
The products IV and VIII, when used as stabilizers for polyolefins, are added to the plastics materials in amounts of, say, from 0.01 to 3% by weight. For example, acid amines VI are used as stabilizers are polyolefins in amounts of from 0.05 to 0.2% by weight, based on the total weight (see Example 9 below). For further information on its use in polyolefins, reference is made to German Patent application P 23 09 431.7).

In the following Examples the parts are by weight unless otherwise stated. The parts by weight relate to the parts by volume as do kilograms to liters.

EXAMPLE 1

To 35 parts of 4-(m,m'-di-t-butyl-p-hydroxyphenyl)-butan-2-ol and 100 parts by volume of pyridine there are added, slowly, 42.5 parts of palmitoyl chloride at 25° C. The mixture is held at this temperature for 3 hours and is then poured onto ice, acidified with 40 parts of HCl and extracted with 200 parts of benzene. The benzene is then distilled off and the residue of the extract is distilled in vacuo. There are obtained 55 parts (84.5% of theory) of 4-(m,m'-d-t-butyl-p-hydroxyphenyl)-butyl-2 ester of palmitic acid, b.p. 254° C/0.01 mm.

EXAMPLE 2

To 111 parts of 2-amino-4-(m,m'-di-t-butyl-p-hydroxyphenyl)-butane and 300 parts by volume of pyridine there are added, slowly, 124 parts of palmitoyl chloride at from 20° to 25° C. The mixture is maintained at this temperature for a further 2 hours. The mixture is then poured onto 1,000 parts of ice, acidified with 100 parts of HCl and extracted with 500 parts of benzene. The benzene is then distilled off and the residue of the extract is distilled in vacuo. There are obtained 143 parts (69.5% of theory) of palmitic 4-(m,m'-di-t-butyl-p-hydroxyphenyl)-butyl-2-amide, b.p. 252° C/0.01 mm.

EXAMPLE 3

To 42 parts of 2-amino-4-(m,m'-di-t-butyl-p-hydroxyphenyl)-butane, 500 parts by volume of benzene and 20 parts of sodium carbonate there are added, over 80 minutes, 21 parts of benzoyl chloride and 100 parts by volume of benzene at from 5° to 10° C. The mixture is held at this temperature for a further 45 minutes, whereupon 20 parts of sodium carbonate are added and the mixture is held at 10° C for a further 3 hours and then heated under reflux for 2 hours. The mixture is filtered hot and the filtrate is concentrated. On cooling, the product crystallizes out. There are obtained 54 parts (93.5% of theory) of benzoic 4-(m,m'-di-t-butyl-p-hydroxyphenyl)-butyl-2-amide, m.p. 140° to 141° C

EXAMPLE 4

To 83 parts of 2-amino-4-(m,m'-di-t-butyl-p-hydroxyphenyl)-butane and 300 parts by volume of pyridine there are added, over 90 minutes, 30 parts of terephthaloyl chloride and 80 parts by volume of benzene at 25° C. The mixture is held at this temperature for 2 hours. It is then poured onto 300 parts of ice. The mixture is then acidified with 40 parts of hydrochloric acid and extracted with 500 parts of benzene. The benzene is removed from the extract by distillation and the product crystallizes out. There are obtained 65 parts (63.5% of theory) of terephthalic di-[4-(m,m'-di-t-butyl-p-hydroxyphenyl)-butyl-2-amide], m.p. 245° to 247° C after recrystallization from 1:1 benzene/methanol.

EXAMPLE 5

To 111 parts of 2-amino-4-(m,m'-di-t-butyl-p-hydroxyphenyl)-butane, 500 parts by volume of benzene and 2 parts by volume of pyridine there are added, slowly, 55 parts of diphenylmethane-4,4'-diisocyanate in 500 parts by volume of chloroform at 25° to 30° C. The mixture is then heated at 40° C for 1 hour and filtered. There are obtained 77 parts (48% of theory) of 4,4'-di-[4'''-(m,m'-di-t-butyl-p-hydroxyphenyl)-butyl-2'''-ureido]-diphenylmethane, m.p. 183° to 186° C after recrystallization from 1:1 benzene/methanol.

EXAMPLE 6

To 107 parts of 2-amino-4-(m,m'-di-t-butyl-p-hydroxyphenyl)-butane, 500 parts by volume of benzene and 2 parts by volume of pyridine there are added 37 parts of hexamethylene dissocyanate at 25° C. The mixture is maintained at 60° C for 15 hours. It is then filtered to give 110 parts (78.5% of theory) of ω)ω'-di-[4-(m,m'-di-t-butyl-p-hydroxyphenyl)-butyl-2]ureidohexane, m.p. 200° to 202° C after recrystallization from 1:1 benzene/methanol.

EXAMPLE 7

To 44 parts of 2-amino-4-(m,m'-di-t-butyl-p-hydroxyphenyl)-butane, 150 parts by volume of benzene and 0.2 part by volume of pyridine there are added, over 15 minutes, 16 parts of p-isocyanatocumyl isocyanate at from 20° to 25° C. The mixture is heated under reflux for 10 minutes and then the benzene is distilled off. The residue is heated at 70° C with 200 parts of cyclohexane and then filtered. There are obtained 57 parts (94% of theory) of N-p-[4-(m,m'-di-t-butyl-p-hydroxyphenyl)-butyl-2-ureidoisopropyl]-phenyl-N-[4-(m,m'-di-t-butyl-p-hydroxyphenyl)-]butyl-2-urea of the formula:

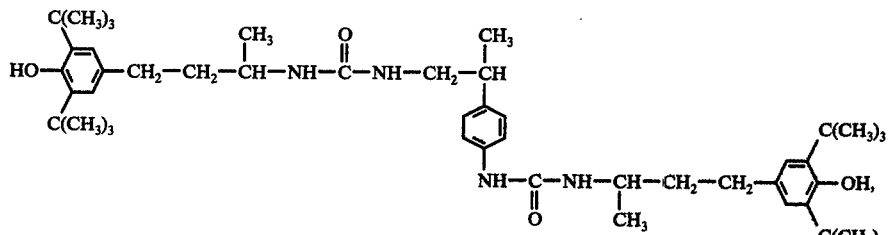

m.p. 40° to 45° C. -(m,m'

EXAMPLE 8

To 28 parts of 2-amino-4-(m,m'-di-tu-butyl-p-hydroxyphenyl)-butane, 100 parts by volume of benzene and 0.2 part by volume of pyridine there are added, over 30 minutes, 12 parts of decahydronaphthalene-1,5-diisocyanate at 25° C. The mixture is heated under reflux for 15 minutes and the benzene is distilled off. There are obtained 30 parts (79.5% of theory) of 1.5-di-[4-(m,m'-di-t-butyl-p-hydroxyphenyl)-butyl-2-ureido-]decahydronaphthalene, m.p. 40° to 45° C.

EXAMPLE 9

Polypropylene is mixed with 0.2% by weight of the palmitic amide of 4-(m,m'-di-t-butyl-p-hydroxyphenyl)-2-aminobutane, based on the total weight, and the mixture is melted. The stabilized polypropylene is then rolled out to panels having a thickness of 1 mm, from which plates measuring 15 × 40 × 1 mm are cut. The plates are suspended in a conditioning chamber through which air is constantly passed at a temperature of 140° C. For comparison, plates of the same size but of unstabilized polypropylene are also suspended in said chamber. The plates are kept in constant motion by mechanical means. In this aging test, the degradation of the polypropylene is tested under stringent conditions. Unlike the unstabilized polypropylene plates, on which signs of degradation may be observed after only a few hours, on oxidation or discoloration of the stabilized polypropylene plates may be observed after a testing period of 450 hours.

EXAMPLE 10

250 parts of 4-(m,m'-di-t-butyl-p-hydroxyphenyl)-butan-2-one are dissolved in 1,000 parts of methanol and hydrogenated in an autoclave at 150° C under a hydrogen pressure of 100 atmospheres, using 50 parts of Raney nickel as catalyst. On completion of the reaction, the methanol is distilled off. The residue is then distilled in vacuo to give 234 parts of 4-(m,m'-di-t-butyl-p-hydroxyphenyl)-butan-2-ol, b.p. 136° C/0.01 mm, equivalent to a yield of 93% of theory.

EXAMPLE 11

Polypropylene is mixed with 0.2% by weight of 4-(m,m'-di-t-butyl-p-hydroxyphenyl)-butan-2-ol, based on the total weight, and the mixture is melted. The stabilized polypropylene is then rolled out to panels having a thickness of 1 mm, from which plates measuring 15 × 40 × 1 mm are cut. The plates are suspended in a conditioning chamber through which air is constantly passed at a temperature of 140° C. For comparison, plates of the same size but of unstabilized polypropylene are also suspended in said chamber. The plates are kept in constant motion by mechanical means. In this aging test, the degradation of the polypropylene is tested under stringent conditions. Unlike the unstabilized polypropylene plates, on which signs of degradation may be observed after only a few hours, no oxidation or discoloration of the stabilized polypropylene plates may be observed after a testing period of 450 hours.

EXAMPLE 12

250 parts of 4-(m,m'-di-t-butyl-p-hydroxyphenyl)-butan-2-one are dissolved in 1,000 parts of methanol and mixed, in an autoclave, with 550 parts of ammonia and 50 parts of Raney nickel and the mixture is then heated at 90° C under hydrogen to give a hydrogen pressure of 100 atmospheres. The mixture is maintained at this temperature for 10 hours. On completion of the reaction, the excess ammonia and the methanol are distilled off. The solid residue is distilled in vacuo at 0.1 mm of Hg. After recrystallization of the distillate from a mixture of cyclohexane and benzene there are obtained 230 parts of 4-(m,m'-di-t-butyl-p-hydroxyphenyl)-2-aminobutane, m.p. 99° to 100° C, equivalent to a yield of 92% of theory.

EXAMPLE 13

Polypropylene is mixed with 0.2% by weight of 2-amino-4-(m,m'-di-t-butyl-p-hydroxyphenyl)-butane, based on the total weight, and the mixture is melted. The stabilized polypropylene is then rolled out to panels having a thickness of 1 mm, from which plates measuring 15 × 40 × 1 mm are cut. The plates are suspended in a conditioning chamber through which air is constantly passed at a temperature of 140° C. For comparison, plates of the same size but of unstabilized polypropylene are also suspended in said chamber. The plates are kept in constant motion by mechanical means. In this aging test, the degradation of the polypropylene is tested under stringent conditions. Unlike the unstabilized polypropylene plates, on which signs of degradation may be observed after only a few hours, no oxidation of discoloration of the stabilized polypropylene plates may be observed after a testing period of 450 hours.

We claim:

1. 4-(m,m'-di-t-butyl-p-hydroxyphenyl)-butyl-2-bisamides of the formula

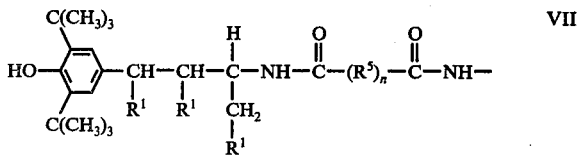

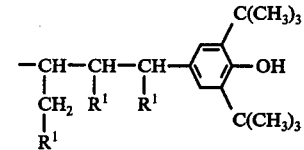

in which each $R^1$ respectively is hydrogen or an aliphatic radical, $R^5$ is an aliphatic, cycloaliphatic, araliphatic, or aromatic radical and $n$ is 0 or 1.

2. Compounds as claimed in claim 1, in which the radicals $R^1$ respectively are hydrogen or alkyl of 1 to 4 carbon atoms, $R^5$ denotes alkylene of 1 to 20 carbon atoms, cyclohexylene, aralkylene of from 7 to 15 carbon atoms, phenylene or naphthylene, optionally wholly or partially hydrogenated, benzylcyclohexylene or benzylphenylene, which radicals may be further substituted by alkyl or alkoxy of 1 to 4 carbon atoms, and $n$ is 0 or 1.

3. Compounds as claimed in claim 1 in which $R^1$ is hydrogen, $n$ is 0 or 1, and $R^5$ is alkylene having 1 to 20 carbon atoms.

4. Compounds as claimed in claim 1 in which $R^1$ is hydrogen, $n$ is 1 and $R^5$ is alkylene having 1 to 6 carbon atoms.

5. Compounds as claimed in claim 1 in which $R^1$ is hydrogen, $n$ is 1, and $R^5$ is cyclohexylene.

6. Compounds as claimed in claim 1 in which $R^1$ is hydrogen, $n$ is 1, and $R^5$ is phenylene.

7. Compounds as claimed in claim 1 and selected from the group consisting of compounds having the formulae:

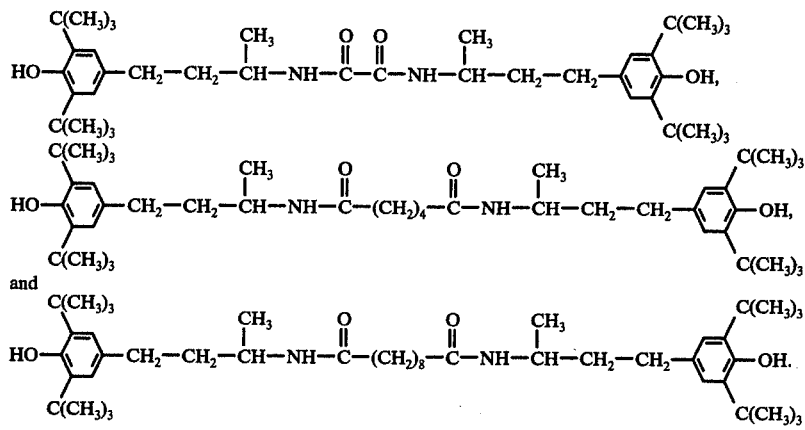

8. Compounds as claimed in claim 1 and selected from the group consisting of compounds having the formulae:

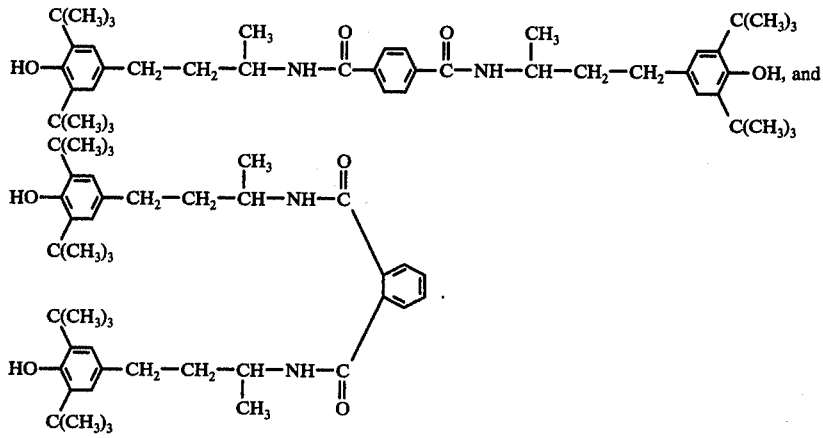

9. Compounds as claimed in claim 1 in which each $R^1$ is hydrogen and $R^5$ represents the divalent radical of a dicarboxylic acid selected from the group consisting of oxalic acid, malonic acid, succinic acid, glutaric acid, adipic acid, pimelic acid, sebacic acid, decanedioic acid, terephthalic acid, cyclohexane-1,4-dioic acid, cyclohexane-1,2-dioic acid, cyclohexane-1,3-dioic acid, naphthalene-1,4-dioic acid, naphthalene-1,8-dioic acid, isophthalic acid, phthalic acid, diphenylmethane-4,4'-dioic acid, 4-(p-carboxybenzyl)-cyclohexanoic acid, tetrahydronaphthalene-1,8-dioic acid, tetrahydronaphthalene-1,5-dioic acid, decahydronaphthalene-1,8-dioic acid, decahydronaphthalene-1,5-dioic acid, p-(1-carboxypropyl-2)-benzoic acid, p-(carboxymethyl)-benzoic acid and p-(carboxymethyl)-phenylacetic acid.

* * * * *